US006132959A

United States Patent [19]

Blake

[11] Patent Number: 6,132,959
[45] Date of Patent: Oct. 17, 2000

[54] METHOD FOR EARLY DETECTION OF HIV INFECTION IN BABIES

[75] Inventor: Milan Blake, New York, N.Y.

[73] Assignee: Blake Laboratories, Inc., Great Neck, N.Y.

[21] Appl. No.: 09/084,456

[22] Filed: May 26, 1998

Related U.S. Application Data

[63] Continuation of application No. 08/920,627, Aug. 27, 1997, abandoned, which is a continuation of application No. 08/473,847, Jun. 7, 1995, abandoned.

[51] Int. Cl.[7] .................................................. C12Q 1/70
[52] U.S. Cl. ............................. 435/5; 435/7.1; 435/7.7; 435/7.72; 435/7.9; 435/7.91; 435/7.92; 435/7.93; 435/7.94; 435/7.95; 435/974; 435/975
[58] Field of Search .............................. 435/5, 7.1, 7.7, 435/7.72, 7.9, 7.91, 7.92, 7.93, 7.94, 7.95, 974, 975; 530/350

[56] References Cited

U.S. PATENT DOCUMENTS 4,757,134  7/1988  Blake et al. .............................. 530/350

FOREIGN PATENT DOCUMENTS 9518973  7/1995  WIPO .

OTHER PUBLICATIONS

Rossi, P. et al. (1992) Early diagnosis of HIV infection in infants. Journal of Acquired Immune Deficiency Syndromes 5(11): 1169–1178.

Rogers, M.F. et al. (1991) Advances and problems in the diagnosis of human immunodeficiency virus infection in infants. Pediatr. Infect. Dis. J. 10(7): 523–531.

Husson, R.N. et al. (1990) Diagnosis of human immunodeficiency virus infection in infants and children. Pediatr. 86(1): 1–10.

European Collaborative Study (1991) Children born to women with HIV–1 infection; natural history and risk of transmission. The Lancet 337(8736): 253–260.

Re, M.C. et al. (1992) Immunoblotting Analysis of IgA and IgM Antibody to Human Immunodeficiency Virus Type 1 (HIV–1) Polypeptides in Seropositive Infants. Eur. J. Clin. Microbiol. Infect. Dis. 11(1):27–32.

Portincasa, P. et al. (1992) Detection of IgA and IgM antibodies to HIV–1 in neonates by radioimmune western blotting. BMJ 304: 1539–1542.

Russell–Jones, G.J., Gotschlich, E.C., Blake, M.S. (1984) A Surface Receptor Specific for Human IgA on Group B Stroptococci Possesing the Ibc Protein Antigen. J. Exp. Med. 160: 1467–1475.

Landesman, S. et al. (1991) Clinical Utility of HIV–IgA Immunonoblot Assay in the Early Diagnosis of Perinatal HIV Infection. JAMA 266(24): 3443–3446.

Kline, M.W. et al. (1994) A comparative study of human immunodeficiency virus culture, polymerase chain reaction and anti–human immunodeficiency virus immunoglobulin A antibody detection in the diagnosis during early infancy of vertically acquired human immunodeficiency virus infection. Pediatr. Infect. Dis. J. 13(2): 90–94.

Quinn, T.C. et al. (1991) Early Diagnosis of Perinatal HIV Infection by Detection of Viral–Specific IgA Antibodies. JAMA 266(24): 3439–3442.

Martin, N.L. et al. (1992) A Screening Test for the Detection of Anti–HIV–1 IgA in Young Infants. Immunological Investigations 21(1): 65–70.

Moss, D.W. et al. (1985) An enzyme–amplified monoclonal immunoenzymometric assay for prostatic acid phosphatase. Clinica. Chimical. Acta. 152: 85–94.

Johannsson, A., Stanley, C.J., Self, C.H. (1985) A fast highly sensitive colorimetric enzyme immunoassay system demonstrating benefits of enzyme amplification in clinical chemistry. Clinica. Chimical. Acta. 148: 119–124.

Self, C.H. et al. (1985) A New Sensitive and Fast Peptide Immunoassay Based on Enzyme Amplification Used in the Determination of CGRP and the Demonstration of its Presence in the Thyroid. Peptides 6: 627–630.

Coates, R.A. et al. (1992) Using Serial Observations to Identify Predictors of Progression to AIDS in the Toronto Sexual Contact Study. J. Clin. Epidemiol. 45(3): 245–253.

Tache, S. (1995) Delay and Limited HIV IgA Production in In–utero Vertically HIV–1 Infected Infants with Rapid Disease Progression Compared to Infants Infected Intrapartum with Slow Disease Progression. Abstract presented on Southern or Western Regional meeting of the American Federation for Clinical Research. Journal of Investigative Medicine, Feb. 2–4 and Feb. 8–11 in New Orleans, LA and Carmel, CA (Abstract).

Lombardi, V. et al. (1993) Early detection of IgA specific antibodies in HIV–1 infected children by peptide–ELISA and peptide time–resolved fluoro–immunoassay. Eur. J. Pediatr. 152: 484–489.

Connor, E. et al. (1993) Enzyme Immunoassay for Detection of Human Immunodeficiency Virus–Specific Immunoglobulin A Antibodies. Journal of Clinical Microbiology 31(3): 681–684.

Connell, J.A. et al. (1992) HIV Antibodies in Babies (letter; comment). BMJ 305(6849): 367.

Johnson, J.P. et al. (1989) Natural History and Serologic Diagnosis of Infants Born to Human Immunodeficiency Virus–Infected Women. American Journal of Diseases in Children 143(10): 1147–1153.

Schüpbach, J. et al. (1994) IgG, IgM and IgA Response to HIV in Infants Born to HIV–1 Infected Mothers. Journal of Acquired Immune Deficiency Syndromes 7: 421–427.

(List continued on next page.)

Primary Examiner—Jeffrey Stucker
Attorney, Agent, or Firm—Saliwanchik, Lloyd & Saliwanchik

[57] ABSTRACT

Disclosed and claimed is a novel inexpensive and efficient method for the early detection of HIV infection in babies. The method utilizes a unique IgA capture ELISA procedure for detection of HIV-specific antibodies.

12 Claims, No Drawings

OTHER PUBLICATIONS

Reed, S. et al. (1993) Vertical Transmission of HIV in the Bahamas. IXth International Conference on AIDS (#PO–B05–1034), Abstract Only.

Matsueda, S. et al. (1993) Characteristics of IgA antibodies against HIV–1 in sera and saliva from HIV–seropositive individuals in different clinical stages. Scand. J. Immunol. 38(5): 428–434, Chemical Abstracts 120: 822, Abstract No. 215097u.

Quesnel, A. et al. (1993) Prognostic value of serum immunoglobulin A antibodies to pol gene products during HIV–1 infection. Clin. Exp. Immunol. 91(2): 237–240, Chemical Abstracts 119: 724, Abstract No. 201584t.

Weiblen, G. et al. (1990) Detection of IgM and IgA HIV antibodies after removal of IgG with recombinant protein G. J. Immunol. Methods 126: 199–204, Chemical Abstracts 112(25): 458, Abstract No. 233577q.

Faulmann, E.L. et al. (1991) Protein B: a versatile bacterial Fc–binding protein selective for human IgA. Bio Techniques 10(6): 748–750, Chemical Abstracts 115(23): 616, Abstract No. 253455p.

George, J.R. et al. (1993) Detection of HIV–1 IgA by an IgA Capture Enzyme Immunoassay for Early Diagnosis in Infants. Annals of the New York Academy of Sciences 693: 272–274.

Berry, N.J. et al. (1991) A comparison of four enzyme immunoassays for the simultaneous detection of HIV–1– and HIV–2–specific antibody. Journal of Virological Methods 34: 91–100.

Renom, G. et al. (1990) Detection of Anti–HIV IgA in Tears of Children Born to Seropositive Mothers is Highly Specific. Res. Virol. 141: 557–562.

Livingston, A. et al. (1994) HIV–Specific IgA in Infants Born to HIV Seropostive Women. Pediatric AIDS and HIV Infection 5(5):321 (Unnumbered Abstract).

Liberatore, D. et al. (1994) Diagnosis of Perinatally Acquired HIV–1 Infection by IgA EIA Test. International Conference on AIDS 10(1): 255, Abstract No. PB0450.

Faulmann et al., "Brotein B: A Versatile Bacterial Fc–Binding Protein Selective for Human IgA", *BioTechniques*, vol. 10, No. 6 (1991), pp. 748–750.

Cruse et al. Editors of *Illustrated Dictionary of Immunology*, CRC Press Inc., p. 250.

METHOD FOR EARLY DETECTION OF HIV INFECTION IN BABIES

CROSS-REFERENCE TO RELATED APPLICATIONS

This is continuation of application Ser. No. 08/920,627, filed Aug. 27, 1997 abandoned; which is a continuation of application Ser. No. 08/473,847, filed Jun. 7, 1995, now abandoned.

BACKGROUND OF THE INVENTION

The early detection of HIV infection in babies born to HIV infected mothers is very important for disease management, as well as interventional and psychosocial reasons. Although identification of the presence of HIV through in vitro culture of the virus, polymerase chain reaction (PCR) amplification of HIV nucleic acid sequences, and/or identification of HIV p24 antigen is the most definitive approach (1–3), these techniques are expensive and not widely available, particularly in developing countries.

The standard IgG antibody-based assays for HIV detection are not useful for early detection of HIV infection in babies because of the maternal antibodies present in babies blood. The presence of maternal antibodies can be detected up to 18 months or more postpartum in an infant's blood using most ELISA assays and immunoblot methods (4, 5). Moreover, there is some variation in the timing of detection or seroreversion, depending on which commercial ELISA assay system is used. However, the mean time to seroreversion in HIV negative babies (i.e., the reversion from being HIV antibody positive to HIV antibody negative) using the most sensitive ELISA kit available is 13.5(±3.5) months using serum and 5.5(±2.5) months using elution of dried blood spots (6).

Since it has been the general belief that maternal IgA and IgM antibodies do not cross the placenta, studies have been carried out to determine the usefulness of HIV-specific IgA and IgM class antibodies in early detection of infection. It has been suggested that HIV-IgA antibodies may cross the placenta (22). However, the procedures used in the studies carried out to date lack the sensitivity required for early diagnosis of HIV infection in infants (7–9). Thus, there remains a need for a sensitive assay method to detect HIV-IgA antibodies present in neonatal blood serum during the first few month of a child's life.

BRIEF SUMMARY OF THE INVENTION

The subject invention concerns a very sensitive and reliable method for early detection of HIV infection in babies. Specifically, the subject invention concerns a very sensitive method for detection of HIV-specific IgA antibodies in biological samples from a child or infant. The detection of these antibodies is at certain times after birth evidence of the presence of HIV infection in an infant.

More specifically, the method of the subject invention comprises:

(1) contacting an immunoabsorbent coated with a protein having a high specific affinity for human IgA (exemplified herein is recombinant protein B) with the serum of a baby; and, (2) detecting HIV-specific antibodies with an HIV-1/2 polypeptide conjugate that is operably linked to a signal generating system such as alkaline phosphatase.

An amplification system can be used to increase the sensitivity of the assay method.

DETAILED DESCRIPTION OF THE INVENTION

Disclosed herein is a unique IgA capture ELISA procedure for detection of HIV-specific IgA antibodies. In a preferred embodiment of the subject method, microtitre plates were coated with recombinant protein B, instead of the frequently used polyclonal antihuman IgA antibodies. Protein B is a surface receptor expressed on group B streptococci possessing the Ibc protein antigen(s). Protein B has a high specific binding affinity for human IgA, with the ability to bind to the Fc region of monomeric or polymeric IgA (10). Other proteins having a high specific affinity for human IgA are known in the art and can be used instead of protein B. Examples of such proteins include purified native protein B, and high affinity monoclonal antibodies that are specific to human IgA. The HIV-specific IgA antibodies captured using the subject assay method can be detected using HIV-1 and HIV-2 polypeptides (referred to herein as HIV-1/2) that are operably linked to a signal generating system that generates a detectable signal under certain conditions. Any signal generating system that generates a detectable signal is contemplated for use with the subject invention. Many such systems are known in the art and include signal systems based on radioactivity, fluorescence, light emission or absorption, and chemiluminescence. In a preferred embodiment, the procedure of the subject invention utilizes alkaline phosphatase conjugated HIV-1/2 peptides to generate a signal used to detect the HIV-specific IgA captured in the assay. The high specificity of this assay was demonstrated by the negative results obtained on all the samples from infants born to seronegative mothers.

The sensitivity of the subject assay can be increased using an "enzyme amplification" technique (15–17). Compared with the conventional assays that utilize alkaline phosphatase alone, the enzyme amplification methodology increases assay sensitivity by 150 to 300 times, and is approximately 50 times more sensitive than common RIA methods (17).

The HIV-IgA antibodies detected by the assay of the subject invention exhibit behavior similar to HIV-IgG transplacental antibodies. From their presence early in life and their decline with increasing age of the uninfected, seroreverting infants, it was inferred that these antibodies originated from the infected mothers and, thus, cross the placenta. In the HIV-infected infants, the decline of maternal antibodies overlaps with the subsequent generation of the baby's own antibodies, the result being that total HIV-IgA antibody levels reach a nadir in the infants at between 2 to 4 months of age. In some infants, HIV-IgA production is delayed and, thus, there is a period when no HIV-IgA antibodies can be detected.

Of the babies who had one or more samples that were negative for HIV-IgA antibodies, all had a negative test within the first 3 months of life. This suggests that their mothers had very low levels of HIV-IgA antibodies and, therefore, very little antibody crossed the placenta and that the babies were not producing HIV-IgA antibodies at this time. In adults, levels of total IgA antibody generally increases as HIV infection progresses to disease (18). However, this may not reflect increases in specific HIV-IgA antibody. Three of the four babies showed evidence of subsequent production of their own HIV-IgA antibody. Three of the babies developed disease early on and died by 7 months of age. This suggests that the virus is transmitted to the infant during gestation rather than at the time of delivery (19).

Passively transferred HIV-IgA antibodies cannot be detected using conventional HIV-IgA antibody ELISA tests (20, 21). This indicates that the quantity of HIV-IgA antibodies that cross the placenta must be considerably less than the quantity of HIV-IgG antibodies, as one would expect. This also means that HIV-IgA antibodies would be lost sooner than the HIV-IgG antibodies. This is supported by the results disclosed herein that the specificity of detection of uninfected seroreverting babies is 100% by 8 months of age. This is at least 6 months earlier than the mean time to HIV-IgG seroreversion using ELISA systems currently available.

Factors affecting the integrity of the placenta such as syphilis or crack cocaine use may affect passive transfer of maternal antibodies. Since the incidence of syphilis and crack cocaine use in pregnancy is high in the Bahamas, compared HIV-IgA levels in HIV infected babies born in Canada were compared to those born in the Bahamas. There were no differences in levels of HIV-IgA in these two groups.

Using the very sensitive and specific assay system described herein for the detection of HIV-IgA antibodies, it was shown that there is passive transfer of these antibodies across the placenta from HIV infected mothers to their babies. These passive antibodies are no longer detectable in HIV uninfected babies by 8 months of age.

Following are examples which illustrate the invention:

Materials and Methods:

Samples from 56 babies born to HIV infected mothers in Nassau, Bahamas and 9 babies born to HIV infected mothers in Toronto, Canada were used. Sequential blood samples were obtained as soon as possible after birth and every 3 to 6 months thereafter until 24 months of age unless the child prior to 24 months of age. Control samples were obtained from 12 babies born to HIV negative mothers in the Bahamas (tested serially) and from 7 cord blood samples from HIV negative mothers delivering in Toronto.

The HIV status of each baby was determined by HIV-1 PCR nucleic acid amplification and viral culture. A baby was considered HIV infected if one or both of the tests was positive on two separate occasions. A baby was considered negative if at least 4 samples taken at different times each were determined to be negative in both assay methods.

The subjects were divided into three groups:

(A) Babies born to HIV negative mothers
 (i) 12 babies born to seronegative mothers in the Bahamas with a total of 25 serial samples.
 (ii) 7 cord blood samples collected in Toronto from HIV negative mothers.
(B) Uninfected babies born to HIV infected mothers
 (i) 37 babies from the Bahamas with 200 serial samples
 (ii) 7 babies from Toronto with 21 serial samples.
(C) HIV-1 infected babies.
 (i) 19 HIV-1 infected babies from the Bahamas with a total of 79 serial samples.
 (ii) 2 babies from Toronto with 6 serial samples.

Detection of HIV Infection: All the samples collected were tested by both viral culture, PCR amplification, and HIV-p24, using standard procedures. Serological profiles were established for each sample, including: an ELISA screening test using HIV-1/2 peptide (referred to herein as IAF, Biochem Immuno Systems, Montreal, Canada), confirmatory ELISA assays using recombinant HIV-1 proteins (referred to herein as CBC, Cambridge Biotech Corp., Worchester, Mass.) and an in-house immunoblot using HIV-1 viral lysate (Cambridge Biotech Corp., Worchester, Mass.). All plasma samples were stored at $-70°$ C. until analyzed.

HIV-IgA Detection: HIV-IgA antibodies were detected using a modified IgA antibody-capture enzyme-linkedimmunoabsorbentassay (ELISA). Briefly, 100 $\mu$l of diluted serum samples (1:200) was pipetted into the wells of a microtitre plate coated with recombinant protein B (Blake Biotechnologies, Boston, USA). HIV-1 positive and negative control sera from adults were included in each plate as controls. All samples were assayed in duplicate. The plate was incubated at room temperature for two hours, and then washed 5 times with 10 mM Tris-buffered saline (pH 8.0) containing 0.05% Tween-20. Subsequently, 50 $\mu$l of HIV-1/2 peptide-alkaline phosphatase conjugate (Murex Diagnostics Ltd., Dartford, UK) was added to each well. The plate was incubated for one hour at $37°$ C. in a humidified chamber, washed 5 times as above, and the bound HIV-1/2 peptide conjugated with alkaline phosphatase was detected by the addition of 50 $\mu$l NADP$^+$ solution (0.2 mM NADP$^+$ in 50 mM diethanolamine, 0.1 mM MgCl$_2$ at pH 9.5), followed by incubation at room temperature for 20 minutes. Subsequently, 100 $\mu$l of amplifier solution (prepared as 62 $\mu$/ml alcohol dehydrogenase, 1 $\mu$/ml diaphorase, 1 mM INT-Violet (Sigma Chemical Co.) in 25 mM phosphate buffer (pH 7.0) with 3% (v/v) ethanol) was added to the wells of the microtitre plate and the plate was incubated for 5 to 10 minutes at room temperature until the absorbance of the positive control reached or exceeded 2.0 O.D.$_{492}$ The colour development was then stopped by the addition of 50 $\mu$l of 1 N sulfuric acid. The light wavelength absorbance was immediately measured at 492 nm for each well of its plate.

The ratio of optical density (O.D.$_{492}$) of each well to the cut-off value (C.O.) was used to calculate the results. The cutoff value was based upon the average of the negative controls run on each plate plus 3 standard deviations. Samples that had O.D.$_{492}$ values higher than that of C.O. were considered negative.

Results: No HIV-IgA antibodies were detected in 25 samples obtained from the 12 babies born to seronegative mothers from the Bahamas. This was also true for the 7 cord blood samples collected in Toronto. The mean ratio of O.D./C.O. was 0.65 ($\pm$0.08). The specificity of the subject assay in this group was 100%. All the Bahamian infants had samples tested within the first 2 months after the infant was born.

Two hundred and twenty-one samples from 44 uninfected babies born to seropositive mothers were tested. All 71 samples taken within the first three months of life (1–3 samples per baby) tested positive for HIV-IgA antibodies (100%). Beginning at about the fourth month of age, the percentage of samples testing negative for HIV-IgA antibodies increased: at 4 months, 11% (2 out of 18) tested negative; at 5 months, 22% (2 out of 9); at 6 months, 36% (5 out of 14) and finally at 7 months, 91% (10 out of 11) samples tested negative. All samples collected at the eighth month of age and older tested negative (100%) for HIV-IgA. The mean time to seroreversion for these uninfected babies is 6.6 ($\pm$1.8) months. The correlation between the decline of O.D/C.O. ratio and the babies' age is statistically significant (r=0.93; p<0.005).

Of eighty-five samples taken from 21 HIV-1 infected babies, eighty were positive for HIV-IgA (94%). The 5 specimens in this group with no detectable HIV-IgA antibodies were collected at less than 3 months of age from four Bahamian infants. All 5 specimens were strongly positive for HIV-IgA/IgM antibodies by ELISAs (IAF & CBC) and immunoblot. Three of these babies died before 7 months of age. HIV-IgA antibodies were not detectable in two sequential specimens taken from one baby who died at the age of 4 months. One baby who died at 7 months was HIV-IgA antibody negative at birth, but was weakly positive at 2 months and 6 months. The other 2 negative results were obtained on samples collected at 2 months of age from 2 different babies. Both babies were initially positive for HIV-IgA antibodies. Positive results were again obtained on the third samples for both babies. There is no statistical correlation between the ratio of O.D./C.O. and the babies' age in the total group of HIV-1 infected babies (r=+0.22; 0.25>p>0.10). However, 5 individual profiles of HIV-IgA showed a substantial drop in O.D/C.O. ratio at the age of 3 to 4 months. Statistical analysis of all HIV infected children by variance (ANOVA) shows that significant differences exist when comparing the mean values of O.D/C.O. for specimens collected at 3 to 4 months of age with that of specimens collected at other months (p<0.05).

The overall detection rate of HIV-IgA antibodies in the placenta samples collected during the first 3 months of age from babies born to HIV-infected women was 95.4% (104/109). Using the assay of the subject invention, the predictive value of a positive result or a negative result after 8 months of age is 100%.

The above results show the presence of HIV-IgA antibodies in 94% of 85 sequential samples from 21 HIV-infected babies and 100% of 71 specimens collected during the first 3 months of life from babies who seroreverted and were found to be uninfected. These results are in contrast to the previous work done by other investigators (11, 12), where HIV-IgA antibodies were only detected in a small number of serum specimens collected from HIV infected babies at birth. Although Quinn et al. (13) studying sera from 47 HIV infected and 243 uninfected children, found that the sensitivity and specificity of an immunoblot assay for HIV-IgA antibodies in children over 6 months of age were 97.6% and 99.7%, respectively, none of the assay procedures employed in these studies could detect passive maternal IgA antibodies in uninfected babies of HIV infected mothers (7, 11, 14). However, the methods employed in the previous studied consisted mainly of immunoblot and dot blot techniques or conventional ELISA (7,1–14), and therefore can not be directly compared to the assay of the subject invention.

The assay method of the subject invention can also be utilized to determine the HIV status of a woman that has given birth to a child. The subject assay, which can be used to detect maternal HIV-IgA antibodies in a biological sample from a newborn, thereby provides the HIV status of the mother. Accordingly, the detection of HIV-IgA antibodies in a newborn of from about 3 to 4 months of age or older using the assay of the subject invention is a diagnostic indication that the mother is infected with HIV.

The subject invention can be used with a number of biological samples obtained from a person, including urine, saliva, etc. In a preferred embodiment, serum from blood is used as the biological sample to be assayed for HIV-IgA antibodies.

The subject invention also concerns a kit comprising certain reagents used in performing the assay method of the subject invention. In a preferred embodiment, the kit may include a reagent that has a high specific binding affinity for human IgA antibodies. The kit may further comprise an HIV-1/2 polypeptide that is operably linked to a signal generating system that is capable of generating a detectable signal under appropriate conditions. For example, one signal generating system may comprise an alkaline phosphatase enzyme conjugate. The kit of the subject invention may also include an amplification system as described herein.

It should be understood that the examples and embodiments described herein are for illustrative purposes only and that various modifications or changes in light thereof will be suggested to persons skilled in the art and are to be included within the spirit and purview of this application and the scope of the appended claims.

REFERENCES CITED

1. Rossi, P., Albert, J., Biberfeld, G., Borkowsky, W., Caniglia, M., DeRossi, A., et al. Report of a consensus workshop. Siena, Italy, Jan. 17–18, 1992; Early diagnosis of HIV infection in infants. J. Acquir Immuno Defic Syndr 1992; 5:1169–78.
2. Rogers, M. F., Ou, C., Kilbourne, B., & Schochetman, G., Advances and Problems in the diagnosis of human immunodeficiency virus infection in infants. Pediatr Infect Dis J. 1991; 10:523–31.
3. Husson, R. N., Comeau, A. M., Hoff, R., Diagnosis of human immunodeficiency virus infection in infants and children. Pediatr. 1990; 86:1–10.
4. The European Collaborative Study. Children born to women with HIV-1 infection; natural history and risk of infection. Lancet. 1991; 2:253–59.
5. Johnson, J. P., Nair, P., Hines, S. E., Seiden, W., Alger, L., Revic, D. P. et al. Natural history and serologica diagnosis of infants born to human immunodeficiency virus-infected women. AIDS. 1989; 143:1147–53.
6. Read S. E., Gomez, P., Major, C., Bain, R., Cassol, S., O'Shaughnessay, M., et al. Vertical transmission of HIV in the Bahamas. IXth International Conference on AIDS, 1993. (#PO-B05-1034).
7. Ro, M. C., Fortini, G., Vignoli, M., Zanti, G., Dallacasa, P., Masi, M. et al. Immunoblotting analysis of IgA and IgM antibody to human immunodeficienty virus type 1 (HiV-1) polypeptides in seropositive infants. Eur J. Clin Microbiol Infect Dis. 1992; 11:27–32.
8. Portinicassa, P., Conti, G., Ro, M. C., Cherzi, C., Detection of IgA and IgM antibodies to HIV-1 in neonatas by radioimmune western blotting. BMJ 1992; 304:1539–42.
9. Schuphach, J., Tomasik, Z., Iendis, J. Boni, J., Seger, R., Kind, C., et al. IgG, IgM, and IgA response to HIV in infants born to HIV-1 infected mothers. AIDS 1994; 7: 421–27.
10. Russell-Jones, E. J., Goochlich, Blake M., A surface receptor specific for human IgA on group B streptococci possessing the Abc protein. Exp. Med. 1984; 160:1467–75.
11. Landesman, S., Weiblen, B., Herman, M., Willoughby, A., Goodert, J. J. Rubinstein, A., et al. Clinical utility of HIV-IgA immunoblot assay in the early diagnosis of perinatal HIV infection. JAMA 1991; 266:3443–46.
12. Kline, M. W., Lewis, D. E., Hollinger, F. B., Reuben, J. M., Hanson, I. C., Kosinetz, C. A. et al. A comparative study of human immunodeficiency virus immunoglobuline A antibody detection in the diagnosis during early infancy of vertically acquired human immunodeficiency virus infection. Pediatr Infect Dis J. 1994; 13:90–4.
13. Quinn, T. C., Kline, R. L., Halsey, N., Hutton, N. Ruff, A., Butz, A., et al. Early diagnosis of perinatal HIV infection by detection of viral-specific IgA antibodies. JAMA 1991; 266:3439–42.
14. Martin, N. L., Rausben, J., Crombleholme, W., Rautosen, N., Wars, D. W. A screening test for the detection of anti-HIV-1 IgA in young infants. Immunol Inv 1992; 21(1):65–70.

15. Moss, D. W., Self, C. H., Whitaker, K. B., Bailyes, B., Siddle, K., Johannson, A., et al. An enzyme-amplified monoclonal immunoenzymomeric assay for prostatic acid phosphatase. Clinica Chimica Acta 1985; 152:85–94.
16. Johannson, A., Stanley, C. J., & Self, C. H., A fast highly sensitive colorimetric enzyme immunoassay system demonstrating benefits of enzyme amplification in clinical chemistry. Clinica Chimica Acta 1985; 148: 119–24.
17. Self, C. H., Wimalawansa, S. J., Johannsson, A., Batas, D. L., Girgis, S. I., & Macintyre, I. A new sensitive and fast peptide immunoassay based on enzyme amplification used in the determination of CGRP and the demonstration of its presence in the thyroid. Peptides, 1985; 6:627–30.
18. Coates, R. A., Farewell, V. T., Raboud, J., Read, S. E., Klein, M., MacFadden, D. K., et al. Using serial observation to identify predictors of progression to AIDS in the Toronto Sexual Contact Study. J Clin Epidemiol 1992; 45(3):245–53.
19. Tache, S., Yuch, F. L., Von Seidlein, L., Garratty, B. & Bryan, Y. Delay and limited HIV-IgA production in in-utero vertically HIV-1 infected infants with rapid disease progression compared to infants infected intrapartum with slow disease progression. Abstract presented on Southern or Western Regional meeting of the American Federation for Clinical Research. Feb. 2–4, 1995, and Feb. 8–11, 1995, in New Orleans, La. and Carmel, Calif.
20. Lombardi, V., Caniglia, M., Scariatti, G., Jaasson, M., Plehari, A., D'Argenio, P., et al. Early detection of HIV-IgA specific antibodies in HIV-1 infected children by peptide-ELISA and peptide time-resolved fluoro-immunoassay. European J. Pediatr. 1993; 152(6): 484–9.
21. Connor, E., Wong, Z., Stephens, R., Holland, B., Palerbo, P., McSherry, G., et al. Enzyme immunoassay for detection of human immunodeficiency virus-specific immunoglobulin A antibodies. J Clin Microb 1993; 31(3):681–4.
22. Connell, I. A., Perry, J. V., Mortimer, P. P., Barns, S. M., Klokke, A., De Rossi, A., Giaquino, C. HIV antibodies in babies [letter; comment] BMJ 1992; 305(6849):367.

What is claimed is:

1. A method for the detection of maternal IgA antibody to HIV in an infant less than about four months of age which comprises the steps of:
   (a) contacting serum of said infant with an immunoabsorbent comprising a protein having a high specific affinity for human IgA, wherein said protein is Protein B; and,
   (b) detecting HIV-specific IgA antibodies bound by said protein on said immunoabsorbent using a polypeptide composition conjugated with a signal generating system, wherein said polypeptide composition comprises polypeptide selected from the group consisting of HIV-1 polypeptide, HIV-2 polypeptide, and both HIV-1 and HIV-2 polypeptide.

2. The method, according to claim 1, wherein the serum is from an infant of about 3 to about 4 months of age.

3. The method, according to claim 1, wherein the serum is from an infant less than 2 months of age.

4. The method, according to claim 1, wherein an amplification system is used to increase the sensitivity of the method.

5. The method, according to claim 4, wherein said amplification system is an enzyme amplification technique.

6. The method, according to claim 5, wherein said enzyme amplification technique comprises NADP as a substrate for said signal generating system, and the enzymes alcohol dehydrogenase and diaphorase.

7. The method, according to claim 1, wherein said Protein B is recombinantly produced.

8. A kit for the early detection of HIV infection in an infant comprising in one or more containers:
   (a) a protein having a high specific binding affinity for human IgA, wherein said protein is Protein B; and
   (b) polypeptide composition conjugated with a signal generating system, wherein said polypeptide composition comprises polypeptide selected from the group consisting of HIV-1 polypeptide, HIV-2 polypeptide, and both HIV-1 and HIV-2 polypeptide.

9. The kit, according to claim 8, wherein said protein B is recombinantly produced.

10. The kit, according to claim 8, further comprising an amplification system.

11. The kit, according to claim 10, wherein said amplification system comprises an enzyme amplification technique.

12. The kit, according to claim 11, wherein said enzyme amplification technique comprises NADP as a substrate for an alkaline phosphatase signal generating system, and the enzymes alcohol dehydrogenase and diaphorase.

* * * * *

UNITED STATES PATENT AND TRADEMARK OFFICE
CERTIFICATE OF CORRECTION

PATENT NO. : 6,132,959
DATED : October 17, 2000
INVENTOR(S) : Milan Blake

It is certified that error appears in the above-identified patent and that said Letters Patent is hereby corrected as shown below:

Column 1, line 63: "HIV-specificantibodies" should read --HIV-specific antibodies--.

Column 2, line 7: "antihuman" should read --anti-human--.

Column 3, line 34: "prior to 24 months" should read --died prior to 24 months--.

Column 4, lines 5-6: "enzyme-linkedimmunoabsorbentassay" should read --enzyme-linked immunoabsorbent assay--.

Column 4, line 60: "O.D/C.O." should read --O.D./C.O.--.

Column 5, line 14: "O.D/C.O." should read --O.D./C.O.--.

Column 5, line 17: "O.D/C.O." should read --O.D./C.O.--.

Column 5, line 41: "studied" should read --studies--.

Column 6, line 36: "immunodeficienty" should read --immunodeficiency--.

Column 6, line 37: "(HiV-1)" should read --(HIV-1)--.

Column 6, line 40: "neonatas" should read --neonates--.

Signed and Sealed this

First Day of May, 2001

Attest:

NICHOLAS P. GODICI

*Attesting Officer*    *Acting Director of the United States Patent and Trademark Office*